United States Patent [19]

Dressler

[11] Patent Number: 4,705,879
[45] Date of Patent: Nov. 10, 1987

[54] LONG-CHAIN ALKYLRESORCINOL PHOSPHITES

[75] Inventor: Hans Dressler, Monroeville, Pa.

[73] Assignee: Koppers Company, Inc., Pittsburgh, Pa.

[21] Appl. No.: 817,899

[22] Filed: Jan. 13, 1986

[51] Int. Cl.[4] ............................................. C07F 9/145
[52] U.S. Cl. ................................... 558/194; 252/49.8
[58] Field of Search .................................. 558/194, 96

[56] References Cited

U.S. PATENT DOCUMENTS 3,493,638  2/1970  Meltsner .............................. 558/194
4,440,696  4/1984  Maul et al. ............................ 558/96

Primary Examiner—Anton H. Sutto
Attorney, Agent, or Firm—Herbert J. Zeh, Jr.; Donald M. MacKay; Daniel J. Long

[57] ABSTRACT

Alkylresorcinol phosphites useful as antioxidants in lubricants and greases are provided of the formula:

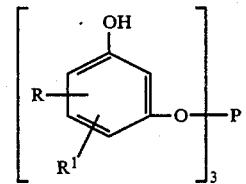

wherein R is selected from H and alkyl, and $R^1$ is an alkyl, said alkyl having from 8 to 18 carbon atoms and consisting of at least 75% secondary alkyl.

10 Claims, No Drawings

LONG-CHAIN ALKYLRESORCINOL PHOSPHITES

FIELD OF THE INVENTION

The invention relates to novel alkylresorcinol phosphites useful as antioxidants for organic materials such as lubricants and greases.

BRIEF DESCRIPTION OF THE PRIOR ART

U.S. Pat. No. 3,467,737 discloses certain tertiary-alkyl-substituted-para-hydroxyphenyl phosphites to be useful as stabilizers for polypropylene and other polymers.

BRIEF DESCRIPTION OF THE INVENTION

It has now been discovered that certain novel long-chain alkylresorcinol phosphites are useful antioxidants, particularly in functional fluids such as lubricants and greases. The novel long-chain alkylresorcinol phosphites are represented by the formula:

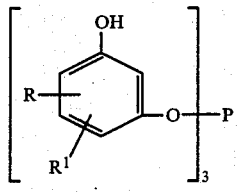

wherein R is selected from H and alkyl, and $R^1$ is an alkyl, the same or different from R, said alkyl having from 8 to 18 carbon atoms and consisting of at least 75% and preferably at least 90% secondary alkyl. The secondary alkyl are preferably attached at its second carbon to the benzene ring and the alkyl are preferably attached to the benzene ring at the 2, 4, or 6 positions. These phosphites are liquids at room temperature and soluble and miscible with functional fluids such as lubricants and greases at room temperature. They can be compounded into organic functional fluid substrates such as alkylated naphthalenes in concentrations between about 0.05 wt. % and about 5.0 wt. % at low temperatures such as 25° C. Moreover, the novel compounds do not separate from hot compounds on cooling. They also have very high thermal stability, high flash points and high fire points.

DETAILED DESCRIPTION OF THE INVENTION

The mono and dialkylresorcinol intermediates can be prepared by the alkylation of resorcinol with alpha-olefins in the presence of a catalyst. The mole ratio of resorcinol to alpha olefin should be from about 0.7 to 1.3 or more in the case of the monoalkylresorcinol and from about 0.4 to about 0.5 in the case of the dialkylresorcinol. The reaction can be conducted at a temperature between about 125° C. and about 250° C., preferably under an inert gas such as nitrogen. Suitable catalysts include the activated clay aluminosilicates and high silica zeolites which are used in an amount from between 10 wt. % and about 100 wt. % based on the resorcinol.

The novel phosphites can be prepared by reacting about three moles of dialkyl or monoalkyl resorcinol with about one mole of phosphorus trichloride preferably with a solvent such as aliphatic and aromatic hydrocarbons such as n-heptane and toluene or a chlorinated hydrocarbon solvent such as methylene chloride, and a catalyst. A catalyst is not required but is preferred. Catalytic amounts of between about 0.1 wt. % and about 5.0 wt. % are employed when the catalyst is utilized. Typical catalysts include triaryl phosphines, pyridine, alkylpyridines and quinolines. Reaction times for the preparation of the novel phosphites are between about 1 and about 12 hours at temperatures of between about 25° C. and about 200° C.

Functional fluids that can be stabilized with the phosphite compounds of the invention include the mono and polyalkylated naphthalenes methyl naphthalenes and dimethyl naphthalenes. Other functional fluids that can be stabilized are, for example, mineral oils, hydrogenated poly(alpha-olefins), and esters.

The following examples will serve to illustrate the invention and preferred embodiments thereof. All parts and percentages in said examples and elsewhere in the specification and claims are by weight unless otherwise specified.

EXAMPLE I (Preparation of mono-$C_{16}$-alkylresorcinol)

A reactor was charged with 440.0 g (4.0 m) resorcinol, 851.2 g (3.8 m) $C_{16}$-alpha-olefin (Gulftene-16) and 220.0 g Filtrol 13-LM (acid clay) catalyst. The stirred mixture, under a nitrogen blanket, was heated to 220° C., held at 220° C. for 1 hr., then cooled and filtered. The filtrate (1,002.1 g, 77.6 wt. % of the organics charged) was stripped to 260° C/1 Torr. The residue, 671.1 g (52 wt. % yield on the organics charged; 67 wt. % yield, corrected for mechanical losses), was an amber viscous oil consisting of a $C_{16}$-alkylresorcinol with an average of 1.6 alkyl groups on the resorcinol ring by IR/NMR analysis. The oil was free of alkene impurities. If desired, pure mono-$C_{16}$-alkyl-resorcinol can be separated from this mixture by fractional distillation.

EXAMPLE II (Preparation of di-$C_{16}$-alkylresorcinol)

A reactor was charged with 110.0 g (1.0 m) resorcinol, 493.0 g (2.2 m) of $C_{16}$-alpha-olefin and 60.3 g Filtrol 13-LM catalyst. The stirred mixture was blanketed with nitrogen, heated to 220° C. in 3 hrs., held at 220° C. for 1 hr., then cooled and filtered. The filtrate (548.0 g, 90.9 wt. % of the organics charged) was stripped to 260° C. (pot)/5 Torr to give 507.0 g (84.1 wt. % yield, based on the organics charged; 92.5 wt. % yield, corrected for mechanical losses) of residue. This residue was an amber, viscous oil consisting largely of di-$C_{16}$-alkylresorcinol (ave. 2.2 $C_{16}$-alkyl groups on the resorcinol ring by IR/NMR analysis), free of alkene impurities.

EXAMPLE III (Preparation of Tris-(3-hydroxy-di-decylphenyl) phosphite)

A reactor was charged with 234.0 g (0.6 m) of di-(decyl) resorcinol (b.p. 221°–240° C./1 Torr; ave. 2.2 $C_{10}$-alkyl groups on the resorcinol ring by IR/NMR analysis), 200 ml. n-heptane and 2.3 g of triphenyl-phosphine as the catalyst. The mixture was heated to 40° C. and 27.5 g (0.2 m) phosphorus trichloride was added dropwise during 15 minutes. Heavy evolution of hydrogen chloride began almost immediately. The mixture was then held, successively, for 0.5 hr. at 40°–41° C., 1 hr. at 70° C., and 3 hrs. at 90° C. while sparging with a stream of dry nitrogen. At the end of this period, the evolution of HCl had ceased. The heptane was distilled off at atmospheric pressure and the product stripped to 200° C. (pot)/1 Torr to give 242.7 g of a pale yellow residue as a viscous oil identified as tris-(3-hydroxy-di-decylphenyl) phosphite, anal. found: 2.6% P; calcd: 2.57% P.

EXAMPLE IV (Preparation of Tris-(3-hydroxy-hexadecylphenyl) phosphite)

A glass reactor was charged with 481.4 g (1.2 m) of mono-$C_{16}$-alkylresorcinol (crude product from ex. 1 above) and 4.8 g triphenylphosphine as the catalyst. To the stirred mixture was added dropwise, at room temperature during 12 minutes 57.8 g (0.42 m) of phosphorus trichloride. The mixture was held for 1 hr. at 28° C., 1 hr. at 40° C., 1 hr. at 70° C. and 2 hrs. at 90° C., with a nitrogen sparge at 90° C. At the end of this period the hydrogen chloride evolution had almost ceased. The charge was now stripped to 265° C. (pot)/1 Torr to give 452.6 g (92% yield) of the hydroxyaryl phosphite as an amber, viscous oil; anal. found: 2.4% P; calcd: 2.2% P.

EXAMPLES V–VII

In accordance with the general procedure of the previous examples, Tris-[3-dihydroxy-di(tetradecyl) phenyl] phosphite (Example V), Tris-[3-hydroxy-di(-hexadecyl) phenyl] phosphite (Example VI), and Tris-[3-hydroxy-di(octadecyl) phenyl] phosphite (Example VII) were prepared.

The compounds of Examples III–VII had the alkyl predominantly attached to the 2,4 or 6 positions on the benzene ring and at least 90% were secondary alkyl attached at its second carbon to the benzene ring.

The thermogravimetric analyses (TGA), flash points, and fire points of the new compounds are shown in Table I.

TABLE I

Thermal Stability and Flammability of the New Phosphites

| Example | Phosphite From Alkylresorcinol | % Wt. Loss by TGA[a], at Temp °C.(°F.) 1% | 3% | 10% | Flash Pt., °C.(°F.) | Fire Pt., °C.(°F.) |
|---|---|---|---|---|---|---|
| III | Di-$C_{10}$—alkylres. | 250(482) | 275(525) | ND[b] | ND[b] | ND[b] |
| IV | Mono-$C_{16}$—alkylres. | 250(482) | 275(525) | 310(590) | 282(540) | 296(565) |
| V | Di-$C_{14}$—alkylres. | 270(578) | 300(573) | 350(662) | 310(590) | ND[b] |
| VI | Di-$C_{16}$—alkylres. | 265(510) | 305(582) | 355(670) | 318(605) | 334(635) |
| VII | Di-$C_{18}$—alkylres. | 320(608) | 350(662) | 390(734) | 321(610) | 334(635) |

[a]Under nitrogen flow; heating rate 20° C./min.
[b]ND = not determined

APPLICATION DATA

The phosphites made from the long-chain alkylresorcinols were effective oxidation inhibitors in a synthetic lubricant oil, as evidenced by much reduced sludge formation at 400° F. The data are summarized Table II.

TABLE II

Oxidation Inhibition by Compounds of the Invention in a Synthetic Oil[a]

| Oxidation Inhibitor | Wt. % Added | Hours to Solidify | % Sludge Formed[b] |
|---|---|---|---|
| None | 0 | 72 | 23.9 |
| III[c] | 1.0 | 150 | 4.9 |
| IV[d] | 1.0 | 120 | 5.6 |
| VI[e] | 1.0 | 100 | ND |
| VII[f] | 1.0 | 100 | 5.3 |
| VII[f] | 2.8 | 100 | 5.7 |

[a]The test oil was a di-$C_{16}$—alkylnaphthalene; 1g. in a small cup was exposed in an air-draft oven at 400° F.
[b]Hexane insolubles.
[c]Tris-[3-hydroxy-di(decyl)phenyl] phosphite
[d]Tris-(3-hydroxy-hexadecylphenyl) phosphite
[e]Tris-[3-hydroxy-di(hexadecyl) phenyl] phosphite
[f]Tris-[3-hydroxy-di(octadecyl) phenyl] phosphite The novel tris-hydroxyaryl phosphites were completely soluble in the oils.

While the above is illustrative of the invention, numerous obvious variations may appear to one of ordinary skill and thus the invention is intended to be limited only by the appended claims.

What is claimed is:

1. Compounds of the formula

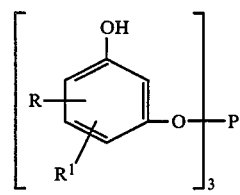

wherein R is selected from H and alkyl, and $R^1$ is an alkyl, said alkyls having from 8 to 18 carbon atoms.

2. The compound of claim 1 wherein the alkyl are attached at its second carbon to the benzene ring.

3. The compound of claim 1 wherein said alkyl are attached to the 2, 4 or 6 positions on the benzene ring.

4. The compound of claim 1 wherein the alkyl is at least 90% secondary alkyl.

5. The compound of claim 1 wherein R and $R^1$ are decyl.

6. The compound of claim 1 wherein R is hydrogen and $R^1$ is hexadecyl.

7. The compound of claim 1 wherein R and $R^1$ are tetradecyl.

8. The compound of claim 1 wherein R and $R^1$ are hexadecyl.

9. The compound of claim 1 wherein R and $R^1$ are octadecyl.

10. A mixture of compounds of claim 1.

* * * * *